United States Patent
Zhang et al.

(10) Patent No.: US 6,759,376 B2
(45) Date of Patent: *Jul. 6, 2004

(54) OIL-CONTAINING PERSONAL WASH LIQUID COMPOSITIONS OR EMULSIONS COMPRISING PARTICLES OF HIGH REFRACTIVE INDEX AND DEFINED THICKNESS, GEOMETRY AND SIZE

(75) Inventors: Xiaodong Zhang, Bloomfield, NJ (US); Pravin Shah, Rutherford, NJ (US); Jennifer Chin, Bloomfield, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/241,401

(22) Filed: Sep. 11, 2002

(65) Prior Publication Data

US 2004/0048757 A1 Mar. 11, 2004

(51) Int. Cl.$^7$ ................................................. A61K 7/00
(52) U.S. Cl. ....................... 510/130; 510/139; 510/159; 510/426; 510/508
(58) Field of Search .................................. 510/130, 139, 510/156, 426, 508, 119, 125, 127, 159; 424/70.9, 70.12, 70.16

(56) References Cited

U.S. PATENT DOCUMENTS

| 3,761,418 A | | 9/1973 | Parran, Jr. |
| 5,312,934 A | | 5/1994 | Letton |
| 5,389,279 A | | 2/1995 | Au et al. |
| 5,952,286 A | | 9/1999 | Puvvada et al. |
| 6,106,816 A | * | 8/2000 | Hitchen ................... 424/70.16 |
| 2002/0085987 A1 | * | 7/2002 | Brown et al. ............ 424/70.11 |
| 2002/0110534 A1 | * | 8/2002 | Fath et al. ................. 424/70.9 |

FOREIGN PATENT DOCUMENTS

| WO | 00/51551 | 9/2000 |

* cited by examiner

Primary Examiner—Necholus Ogden
(74) Attorney, Agent, or Firm—Ronald A. Koatz

(57) ABSTRACT

The invention relates to rinse-off personal care, liquid compositions comprising specifically defined particle wherein compositions also contain at least some hydrophobic benefit agent or emollient. The emollient allows particles to deposit and provide enhanced shine.

4 Claims, No Drawings

OIL-CONTAINING PERSONAL WASH LIQUID COMPOSITIONS OR EMULSIONS COMPRISING PARTICLES OF HIGH REFRACTIVE INDEX AND DEFINED THICKNESS, GEOMETRY AND SIZE

FIELD OF THE INVENTION

The present application relates to oil-containing personal wash, liquid compositions or emulsions, preferably, cleansing, wash-off liquid compositions or emulsions comprising particles having high refractive index (e.g., external surface having refractive index $\geq 1.6$) and defined thickness, geometry and size (e.g., hydrophobically modified mica particles meeting defined parameters). Said particles are delivered, for example, as particle-in-oil liquid emulsion compositions. The particles enhance the shine of skin or other substrate on which they are deposited and reduce the appearance of flaws or defects on the substrate (e.g., skin).

In a second embodiment, the application relates to a method of enhancing skin shine and/or reducing flaws in the appearance of the skin using oil-containing personal wash liquid compositions or emulsions comprising particles as noted above.

BACKGROUND

One of the attributes desired by consumers is shiny, healthy-looking skin. Traditionally, skin "shine" has been achieved by depositions of oils onto substrates (e.g., skin surface). To applicants knowledge, use of specific particles of the invention in oil-containing, rinse-off personal wash liquid compositions (e.g., to enhance shine) is not known. This may be due in part to the inability (prior to subject invention) to deliver such particles in such wash-off, liquid compositions.

The use of particles generally (e.g., mica with green interference color) in personal care compositions is not novel. Thus, for example, International Publication WO 00/51551 (assigned to Procter & Gamble) describes leave-on skin care compositions containing coated mica with green interference color. As indicated the compositions are topical leave-on compositions (see abstract) designed for hand and body rather than liquid compositions of the present invention.

The particles in the WO '551 reference are used as interference particles, not to enhance shine. They have a $TiO_2$ layer thickness in a range of from about 150 nm to about 250 nm (column 6, line 23); this is far smaller than the upper range of thickness claimed for the shine-enhancing particles of the invention (thickness greater than 0.5 microns or 500 nanometers; and greater than the lower range of thickness claimed (thickness of less than or equal to 0.1 micron or 100 nanometers).

Also, the particles of the invention must have a flat, plate-like geometry to ensure shine enhancement. Most critically, perhaps, the reference fails to teach or suggest that the particles must be used in oil-containing, rinse-off, liquid compositions.

Particles having a thickness within the preferred range are also known (Timron® particles) but these particles have also not been used in oil-containing, liquid, personal wash, rinse-off compositions. Further, they have not been hydrophobically modified as is required for particles of the subject invention (i.e., when used in liquids).

Timron® particles sold by EM Industries, for example, are disclosed in a brochure but, as noted, there is no teaching or suggestion in the brochure or any other art that the Timron® product can be used in oil-containing personal wash, liquid, rinse-off compositions to enhance shine. That is, there is simply no disclosure of such particles in oil-containing bars, or in particle-in-oil emulsions used as personal wash compositions.

In summary, pigments used in WO '551 do not recognize the preferred particle thickness or criticality of refractive index; and, where particles of same thickness as those of the invention are known (Timron® products), there is no teaching or suggestion of using these in oil-containing, personal wash, liquid, rinse-off compositions (e.g., to enhance shine).

Unexpectedly, applicants have now found that rinse-off personal wash, liquid compositions (preferably, but not necessarily, surfactant-containing) comprising flat, plate-like particles which particles (outer surface of particles) have a defined refractive index, a preferred thickness and maximum length, and wherein said particles are delivered in compositions/emulsions comprising at least 0.01% to 75% oil provide superior shine compared, for example, to compositions having particles which are delivered in non oil-containing compositions. Further, the particle of the invention must also be hydrophobically modified. While not wishing to be bound by theory, this is believed to help the particle suspend better in oil (e.g., particle suspended in a particle-in-oil emulsion and delivered as an emollient) and be more readily delivered to substrate from the liquid compositions of the invention.

BRIEF SUMMARY OF THE INVENTION

More specifically, the present invention comprises a rinse-off, personal wash, liquid composition comprising:

(1) 0% to 75%, preferably 3% to 65% by weight composition of surfactant;
(2) 0.01% to 20%, preferably 0.02 to 10% by wt. of a particle defined by:
   (a) having an exterior surface which has a refractive index of $\geq 1.6$;
   (b) having a flat, plate-like geometry;
   (c) having a length of particle less than 150 microns; and
   (d) having 0.001% to 5%, preferably 0.0015 to 4% by wt. particle of a hydrophobic modifying agent; and
(3) 0.1% to 75%, preferably 0.5% to 25% by wt., even more preferably 1% to 15% by wt. of a benefit agent or emollient.

In a preferred embodiment, the particle (2) has a thickness of particle (whether hydrophobically modified or not) of greater than or equal to 0.5 microns or less than or equal to 0.1 microns;

In another embodiment, the invention comprises a method of enhancing shine of skin or other substrate using any of the compositions noted above.

DETAILED DESCRIPTION OF THE INVENTION

The present invention relates to compositions for and methods for enhancing shine of skin or other substrate.

More specifically, applicants have found that oil-containing, rinse-off, personal wash, liquid compositions comprising specified platelet-like particles delivered as particle-in-oil liquid emulsions unexpectedly significantly enhance shine as defined by a shine measurement test disclosed herein.

The novel personal wash, liquid compositions of the invention are rinse-off compositions. While not wishing to be bound by theory, it is believed the required oil (e.g., emollient/benefit agent) helps deliver the particles which normally might be expected to readily wash off (providing no shine benefit) from such compositions.

The compositions of the invention comprise:

(1) 0% to 75%, preferably 3% to 65% by wt. of a surfactant or surfactants selected from the group consisting of anionic, nonionic;

(2) 0.01% to 20%, preferably 0.02 to 10% by wt. of particle, wherein the particles are defined by the following characteristics:
   (a) having an exterior surface which has a refractive index greater than or equal to 1.6;
   (b) having flat, plate-like geometry;
   (c) having a particle length less than 150 microns; and
   (d) having 0.001% to 5%, preferably 0.0015% to 4% by wt. particle of a hydrophobic modifying agent; and (3) 0.1% to 75% by wt., preferably 0.5 to 25% by wt. of composition of a benefit agent or emollient.

In a preferred embodiment, particle (2) has a particle thickness (whether or not hydrophobically modified) of greater than or equal to 0.5 microns and less than or equal to 0.1 microns.

Finally, the invention also relates to method of enhancing shine using any of these compositions.

Compositions of the invention are described in greater detail below.

The compositions of the invention are "rinse-off compositions by which is meant that they are intended to be water or rinse-off substrate after applications in contrast to leave-on lotions or cosmetics. The rinse-off compositions are applied as liquid, such as in personal wash liquids.

Surfactants

The compositions of the invention may comprise 0% to 75%, preferably 3% to 65% of a surfactant selected from the group consisting of anionic, nonionic, amphoteric/zwitterionic, cationic surfactant and mixtures thereof.

Among suitable anionic actives which may be used are the alkyl ether sulfates, acyl isethionates, alkyl ether sulfonates, sarcosinates, sulfosuccinates, taurates and combinations thereof. Among suitable amphoteric actives may be included alkylbetaines, amidopropyl betaines, amidopropyl sultaines and combinations thereof.

Alkyl ether sulfates of the present invention will be of the general formula $$R—(OCH_2CH_2)_n OSO_3—M^+$$

wherein R ranges from $C_8–C_{20}$ alkyl, preferably $C_{12}–C_{15}$ alkyl, n is an integer from 1 to 40, preferably from 2 to 9, optimally about 3, and $M^+$ is a sodium, potassium, ammonium or triethanolammonium cation.

Typical commercial co-actives of this variety are listed in the Table below:

| Trademark | Chemical Name | Physical Form | Manufacturer |
|---|---|---|---|
| Steol CS 330 | Sodium Laureth Sulfate | Liquid | Stepan |
| Standopol ES-3 | Sodium Laureth Sulfate | Liquid | Henkel |
| Alkasurf ES-60 | Sodium Laureth Sulfate | Paste | Alkaril |
| Cycloryl TD | TEA Laureth Sulfate | Paste | Cyclo |
| Standopol 125-E | Sodium Laureth-12 Sulfate | Liquid | Henkel |
| Cedepal TD407MF | Sodium Trideceth Sulfate | Paste | Miranol |
| Standopol EA-2 | Ammonium Laureth Sulfate | Liquid | Henkel |

Alkyl ether sulfonates may also be employed for the present invention. Illustrative of this category is a commercial product known as Avenel S-150 commonly known as a sodium $C_{12}–C_{15}$ Pareth-15 sulfonate.

Another active type suitable for use in the present invention is that of the sulfosuccinates. This category is best represented by the monoalkyl sulfosuccinates having the formula $R_2OCCH_2CH(SO_3—Na^+)COO—M^+$; and amido-MEA sulfosuccinates of the formula: $RCONHCH_2CH_2O_2CCH_2CH(SO_3—M^+)COO—M^+$; wherein R ranges from $C_8–C_{20}$ alkyl, preferably $C_{12}–C_{15}$ alkyl and $M^+$ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Emcol 4400-1 | Disodium Lauryl Sulfosuccinate | Solid | Witco |
| Witco C5690 | Disodium Cocoamido MEA Sulfosuccinate | Liquid | Witco |
| McIntyre Mackanate CM40F | Disodium Cocoamido MEA Sulfosuccinate | Liquid | McIntyre |
| Schercopol CMSNa | Disodium Cocoamido MEA Sulfosuccinate | Liquid | Scher |
| Emcol 4100 M | Disodium Myristamido MEA Sulfosuccinate | Paste | Witco |
| Schercopol | Disodium Oleamido MEA | Liquid | Scher |
| Varsulf S13333 | Disodium Ricionoleamido MEA Sulfosuccinate | Solid | Scherex |

Sarcosinates may also be useful in the present invention as a co-active. This category is indicated by the general formula $RCON(CH_3)CH_2CO_2—M^+$, wherein R ranges from $C_8–C_{20}$ alkyl, preferably $C_{12}–C_{15}$ alkyl and $M^+$ is a sodium, potassium ammonium or triethanolammonium cation. Typical commercial products representative of these co-actives are those listed in the Table below:

| Trademark | Chemical Name | Physical Form | Manufacturer |
|---|---|---|---|
| Hamposyl L-95 | Sodium Lauroyl Sarcosinate | Solid | W. R. Grace |
| Hamposyl TOC-30 | TEA Cocoyl/Sarcosinate | Liquid | W. R. Grace |

Taurates may also be employed in the present invention as co-actives. These materials are generally identified by the formula $RCONR'CH_2CH_2SO_3—M^+$, wherein R ranges from $C_8–C_{20}$ alkyl, preferably $C_{12}–C_{15}$ alkyl, R' ranges from $C_1–C_4$ alkyl, and $M^+$ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Igepon TC 42 | Sodium Methyl Cocoyl Taurate | Paste | GAF |
| Igepon T-77 | Sodium Methyl Oleoyl Taurate | Paste | GAF |

Within the category of amphoterics there are three general categories suitable for the present invention. These include alkylbetaines of the formula $RN^+(CH_3)_2CH_2CO_2—M^+$, amidopropyl betaines of the formula $RCONHCH_2CH_2CH_2N^+(CH_3)_2CH_2CO_2^- $—$M^+$, and amidopropyl sultaines of the formula $RCONHCH_2CH_2N+(CH_3)_2CH_2SO_3^-$—$M^+$ wherein R ranges from $C_8$–$C_{20}$ alkyl, preferably $C_{12}$–$C_{15}$ alkyl, and $M^+$ is a sodium, potassium, ammonium or triethanolammonium cation. Typical commercial products representative of these co-actives are found in the Table below:

| Trademark | Chemical Name | Physical Form | Manufacturer |
| --- | --- | --- | --- |
| Tegobetaine F | Cocamidopropyl Betaine | Liquid | Goldschmidt |
| Lonzaine C | Cocamidopropyl Betaine | Liquid | Lonza |
| Lonzaine CS | Cocamidopropyl Hydroxysultaine | Liquid | Lonza |
| Lonzaine 12C | Coco-Betaine | Liquid | Lonza |
| Schercotaine MAB | Myristamidopropyl Betaine | Liquid | Lonza |
| Velvetex OLB-50 | Oleyl Betaine | Paste | Henkel |

Within the broad category of liquid actives, the most effective are the alkyl sulfates, alkyl ether sulfates, alkyl ether sulfonates, sulfosuccinates, and amidopropyl betaines.

Another preferred surfactant is an acyl isethionate having the formula

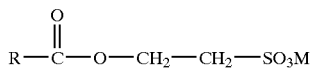

in which R denotes a linear or branched alkyl group and M denotes an alkali metal or alkaline earth metal or an amine.

Another surfactant which may be used are the monoalkyl or dialkylphosphate surfactants.

Another mild surfactant which may be used, preferably used as primary surfactant in combination with other surfactants noted above, is sodium coco glyceryl ether sulfonate. While desirable to use because of its mildness properties, this coco AGS alone does not provide optimum lather creaminess. A sodium 90/10 coconut/tallow alkyl AGS distribution is preferred for creaminess. Salts other than the sodium salt such as TEA-, ammonium, and K-AGS and chain length distributions other than 90/10 coconut/tallow are usable at moderate levels. Also, some soap may be added to improve lather volume and speed of lathering. Certain secondary co-surfactants used in combination with AGS can also provide a creamier and more stable lather. These secondary surfactants should also be intrinsically mild. One secondary surfactant that has been found to be especially desirable is sodium lauroyl sarcosinate (trade name Hamposyl L, made by Hampshire Chemical).

The amphoteric betaines and sultaines noted above can be used as the sole surfactant, but are more preferred as a co-surfactant. Nonionics generally should not be used as the sole surfactant in this product if high foaming is desirable; however, they can be incorporated as a co-surfactant.

Nonionic and cationic surfactants which may be used include any one of those described in U.S. Pat. No. 3,761,418 to Parran, Jr., hereby incorporated by reference into the subject application. Also included are the aldobionamides as taught in U.S. Pat. No. 5,389,279 to Au et al; and the polyhydroxy fatty acid amides as taught in U.S. Pat. No. 5,312,934 to Letton, both of which are incorporated by reference into the subject application.

Soaps may be used at levels of about 0.1 to 10%. Soaps can be used at higher level (for example, to provide soap-like feel) provided that the overall surfactant mixture is milder than soap and retains zein values within the scope of the invention. The soaps may be added neat or made in situ via adding a base, e.g., NaOH; to convert free fatty acids.

A preferred surfactant active system is one such that acyl isethionate comprises 1 to 15% by weight of the total composition and/or an anionic other than acyl isethionate (e.g., ammonium lauryl ether sulfate) comprises 1 to 15% by weight of the total composition and amphoteric comprises 0.5 to 15% by weight of the total composition.

Another preferred active system is one comprising 1 to 20% alkyl ether sulfate. Preferred surfactant systems may also contain 1 to 10% alkali metal lauryl sulfate or $C_{14}$–$C_{16}$ olefin sulphonate instead of acyl isethionate.

Composition Comprising Particle and Oil

One key to the subject invention is that the particles (e.g., $TiO_2$ coated substrate, such as mica, optionally comprising $SiO_2$ or other core) are used in rinse-off, personal liquid wash compositions which must comprise oil. Without wishing to be bound by theory, the oil is believed critical to deposit particle (providing shine) in such rinse-off compositions. The rinse-off, liquid composition of the invention require a hydrophobic surface modifier.

The particle which is used before forming the particle-in-oil compositions is itself defined by the following characteristics:

(a) must have an external surface (whether substrate is solid or has a core) which has a refractive index of $\geq 1.6$ (where refractive index (n) of a substance is defined as $V_v/V$, where $V_v$ is velocity of light in a vacuum and V is the velocity of light in the substance);

(b) must have flat, plate-like geometry;
(This distinction helps distinguish over, for example, the interference pigments of the art which need not be flat);

(c) preferably has a thickness of particle (whether the particle is hydrophobically modified as required in PW liquids or not) of $\geq 0.5$ microns or less than or equal to 0.1 microns;

(d) have a particle length of $<150\mu$.

This is important because the larger particle size can be more obviously seen and therefore, does not provide an aesthetic, uniform appearance which would be generally more desirable to consumers. Also, there may be some issues associated with safety for larger size particles; and (e) have hydrophobic modification of surface (this modification helps ensure deposition of the particle).

Particles such as those described above are similar to those described in a Brochure to Rona® entitled "Special Effect Pigments", published 1998 (except for surface modification).

What neither the brochure, or any other art of which applicants are aware, discloses, however, is use of rinse-off personal wash liquid compositions comprising such particles and benefit agent or emollient (as oil-in-water emulsion in liquid or separate emollient in bar, for example). Specifically, compositions require 0.1% to 75%, preferably 0.5% to 25% by wt. benefit agent for minimal amount of deposition.

Unexpectedly, applicants have found that when emollient is used, it significantly enhances shine of the skin.

Examples of hydrophobic modifying agents which may be used include any of the oils/emollient discussed later herein in connection with the liquid compositions of the subject invention. These include esters (e.g., mono and diesters), fatty acids and alcohols (e.g., palmitic and stearyl alcohols and acids); alkyl polyhydroxyl compounds (e.g., propylene glycol, sorbitol and glycerin); polymeric polyols (e.g., polypropylene glycol and polyethylene glycol); $C_{12}$–$C_{30}$ hydrocarbons (e.g., mineral oil, petrolatum, squalene and isoparaffins).

The hydrophobic modifying agent may comprise 0.001% to 75%, preferably 0.0015% to 4%, by wt. particle.

Liquid Compositions

The liquid products of the invention may be structured using, for example, external structurants such as cross-linked polyacrylates and/or clays or they may be structured with other components (e.g., unsaturated and/or branched long chain $C_8$ to $C_{24}$ liquid fatty acid or ester derivatives) which would cause the liquid to have a "lamellar" structure as described, for example, in U.S. Pat. No. 5,952,286.

The liquid products may have (in addition to surfactant component described previously) other ingredients typically found in liquid formulations. Among these are included (without limitation) auxiliary thickeners (e.g., carboxymethyl cellulose, hydroxyethylcellulose); perfumes; sequestering agents (e.g., ethyl diamine tetra acetate, known as EDTA); coloring agents; opacifiers and pearlizers (e.g., zinc or magnesium stearate, titanium dioxide).

Other optionals include antimicrobial agents; preservatives (e.g., parabens, sorbic acid); suds boosters (e.g., coconut acyl mono- or diethanolamide); antioxidants; cationic conditioners (e.g., Merquat® and Jaguar® type conditioners); polyalkylene glycols, glycerin and other water-soluble conditioning agents; thickeners; exfoliates; ionizing salts; organic acids (e.g., citric or lactic acid).

As noted, the liquid compositions also must contain an oil (emollient).

Emollients are incorporated into the compositions of the present invention at a range from about 0.1 to about 75%, preferably between about 0.5 and 25% by weight of the total composition. Emollients may be classified under such general chemical categories as esters, fatty acids and alcohols, vegetable oils, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate and co-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Vegetable oils include orachis oil, castor oil, cocoa butter, coconut oil, corn oil, cotton seed oil, olive oil, palm kernel oil, rapeseed oil, safflower seed and sesame seed oil, soybean oil.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the liquid compositions of the present invention are thickeners.

A thickener will usually be present in amounts anywhere from 0.1 to 20% by weight, preferably from about 0.5 to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual, functionality.

Various types of active ingredients may be present in compositions of the present invention. Actives are defined as skin benefit agents other than emollients and other than ingredients that merely improve the physical characteristics of the composition. Although not limited to this category, general examples include sunscreens, tanning agents, skin anti-wrinkling agents and anti-acne agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-4 methoxy benzophenone are commercially available under the trademarks, Parsol MCX and Benzophenone-3, respectively. The exact amount of sunscreen employed in the emulsions can vary depending upon the degree of protection desired from the sun's UV radiation.

Additional vitamins may also be included in the compositions of the present invention. Especially preferred is vitamin A palmitate (retinol palmitate) and vitamin E linoleate (tocopherol linoleate). Other esters of vitamins A and E may also be utilized.

Many compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, imidazolidinyl urea, sodium dihydroxyacetate and benzyl alcohol. Preservatives ill usually be employed in amounts ranging from about 0.5% to 2% by weight of the composition.

Powders may be incorporated into the liquid composition of the invention. These powders include chalk, talc, fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

In another embodiment, the invention relates to a method enhancing shine using novel compositions of the invention.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

Methodology

Shine Measurement

All test sites were selected in the volar area of forearms and three sites were chosen from each forearm. For shine measurement, the Charm-view Microscope was used with a 30× magnification lens under the parallel-polarized condition. PhotoSuite III was used to collect images in the bitmap format. A program in IDL was developed to process the captured images and list results in a text file. The average shine intensity for the brightest 10% of the pixels (30720 pixels) was calculated as the shine intensity. First, all sites were washed with Lux®. Baseline images were taken 15 minutes after washing with a Lux® formulation having compositions set forth in Table 1 below. For leave-on application, 11.6 µl of product was applied on test sites with a surface area of 7 cm². The sample was rubbed for about 10 seconds with finger-cot. Images were taken 15 minutes after the product application for initial shine enhancement evaluation. For rinse-off applications, 25 µl of product was applied on test sites with a surface area of 7 cm². The sample was rubbed for about 15 seconds, then left on for 15 seconds followed by a 15 seconds rinsing. Images were taken 15 minutes after the product application for initial shine enhancement evaluation.

Preparation of Thickened Sunflower Seed Oil (TSS)

TSS is a combination of 95 wt. % SSO and 5 wt. % thixcin (rheological additive). SSO was heated to about 85° C., then thixcin was added while mixing with sonicator. When the mixture was cooled down, thixcin formed crystals inside the SSO. As a result, a viscous, shear-thinning oil was obtained.

TABLE 1

| | Lux Shower Cream FORMULATION | | |
|---|---|---|---|
| Chemical or CTFA Name | Level % (100%) | Activity % | Level as Received % |
| Fatty Acids (e.g., Lauric Acid; Myristic Acid; Oleic Acid) | 13–18 | 100.00 | 13–18 |
| Potassium Hydroxide | 4.0 | 90.00 | 4.4 |
| Ethylene Glycol Monostearate | 3.0 | 100.00 | 3.0 |
| Glycerine | 3.0 | 100.00 | 3.0 |
| Betaine | 5.000 | 30.00 | 16.667 |
| Ethylene Diamine Tetraacetic Acid (EDTA) | 0.1 | 50.00 | 0.20 |
| Perfume | 1.000 | 100.00 | 1.0 |
| Sodium Chloride | 1.000 | 100.00 | 1.0 |
| Citric Acid | Minor | 100.00 | — |
| Water | To Balance | 100.00 | — |
| | 100.0 | | 100.0 |

EXAMPLES 1 and 2

Effect of High Refraction Index Coating, Surface Modification and Oil/Mica Interaction In the study below, actives were incorporated into a low surfactant system shower conditioner formulation used as a rinse-off product. The study was to show effect of the particles of the invention (Examples 1 & 2 versus A & B); the effect when using hydrophobically modified particle (Example 2 versus Example 1); and when used with emollient in composition versus no emollient (Example 1 & 2 versus C & D)

Specifically, composition with particle having index below 1.6 (Comparative B) has no additional shine enhancement relative to oil alone (Comparative A) and less shine enhancement than particles of refractive index greater than 1.6 (Examples 1 and 2). Further, the particle which is hydrophobically modified has even more shine (Example 2 versus 1).

The following formulations were tested.

TABLE 2

| | Formulation with Different Actives | | | | | |
|---|---|---|---|---|---|---|
| | Comparative A | Comparative B | Example 1 (Surfactant; Particle w/o Oil) | Example 2 (Surfactant; Particle w/ Oil) | Comparative C | Comparative D |
| Thickened Sunflower Seed Oil | 5 | 5 | 5 | 5 | 0 | 0 |
| Mica (Silk Mica; Index Less Than 1.6) | 0 | 0.25 | 0 | 0 | 0 | 0 |
| High Index $TiO_2$-Coated Mica (Timiron MP 1001) | 0 | 0 | 0.25 | 0 | 0.25 | 0 |
| Surface Modified $TiO_2$-Coated Mica (Timiron MP 1001-AS) | 0 | 0 | 0 | 0.25 | 0 | 0.250 |
| Carbopol | | | | 0.25 | | |
| Alkyl Polyglucoside (Surfactant) | | | | 1 | | |
| Water | | | Add to 100 | | | |
| Shine Enhancement | 10 | 9 | 16 | 23 | 4 | 5 |

From Table 2, it can be seen that Sample B (using mica, which does not have a high refraction index coating) does not provide additional shine enhancement over Sample A (oil only). When mica is coated with high refraction index material such as $TiO_2$, a significant increase in shine enhancement is observed (Example 1 versus Comparative B). If the $TiO_2$-coated mica surface is hydrophobically modified with C14, a further increase in shine enhancement can be achieved (Example 2). However, if the coated mica without surface modification were used without oil in the formulation, the shine enhancement ability is dramatically reduced (Comparatives C and D). This example demonstrates that the importance of high refraction index coat, surface modification and oil/mica combination.

EXAMPLE 3

High Surfactant System: Effect of $TiO_2$-Coated Mica

In this example, surface modified $TiO_2$-coated mica (Timiron MP 1001 AS) was incorporated into a shower gel system. This formulation contains 8.5% sodium lauryl ether sulfate (SLES) (Steol 330); 4.5% CAPBet (zwitterionic surfactant); 10% Timiron MP 1001AS/Amber wax/oil (10/20/70 ratio) and 1% Carbopol. This formulation provides a shine enhancement of 44 which is easily observable visually.

In other words, the high refractive index particles enhance shine even in a high surfactant system.

EXAMPLE 4

Sensory Study of Shower Conditioner Formulations with/without $TiO_2$-Coated Mica In this example, the shine enhancement ability of the surface modified $TiO_2$-coated mica (Timiron MP 1001AS of Example 2) was evaluated by panelists instead of instrument.

A difference test with 60 trials was conducted to investigate the effects of $TiO_2$-coated mica in washing off applications. 5% thickened SSO shower conditioner (Sample A) was used as a vehicle. Six subjects were recruited. Each subject washed forearms with these two samples: vehicle or vehicle with Timiron MP 1001AS (Example 2). Sample A and Example 2 were used on the panelists left and right arm respectively. Forty minutes after product application, ten evaluators were asked to choose from one of the three options: left arm has more shine, right arm has more shine or there is no difference in shine between two arms. Assuming each of the options has ⅓ chance to be chosen as guessing, the number selecting mica as delivering more shine out of 60 trials was significant at $P<0.001$ level.

TABLE 3

Sensory Evaluation of Effect of Timiron MP 1001 AS

|  | Percentage (40 Min) |
|---|---|
| Sample A | 0.23 |
| Example 2 | 0.66 |
| No difference | 0.17 |

The results showed that clearly Timiron MP 1001 AS was an efficient material in adding more shine just after one wash off application.

The examples basically show that in a sample population, consumers preferred hydrophobically modified mica to about almost 3 to 1 (0.66 versus 0.23).

What is claimed is:

1. A liquid personal wash composition comprising:
   (1) 0% to 75% by weight composition surfactant;
   (2) 0.01% to 20% by wt. of a particle defined by:
      (a) an exterior surface having a refractive index $\geq 1.6$;
      (b) having a flat, plate-like geometry;
      (c) having a length of particle <150μ; and
      (d) having 0.001% to 5%, by wt. of a hydrophobic surface modifying agent to help particle suspend better in benefit agent and thereby be more readily delivered to a substrate from said liquid; and
   (3) 0.01% to 75% by out of a hydrophobic benefit agent or emollient in which particle (2) is suspended.

2. A composition according to claim 1, wherein particle (2) has a thickness of particle greater than or equal to 0.5 microns or less than or equal to 0.1 microns.

3. A composition according to claim 1 having 0.0015 to 4% by wt. particle as component (d).

4. A composition according to claim 1 having 5% to 65% by wt. benefit agent of emollient (3).

* * * * *